United States Patent
Kern

(10) Patent No.: US 8,520,802 B2
(45) Date of Patent: Aug. 27, 2013

(54) METHOD FOR DETERMINING THE QUANTITATIVE COMPOSITION OF A POWDER SAMPLE

(75) Inventor: Arnt Kern, Wörth (DE)

(73) Assignee: Bruker AXS GmbH, Karlsruhe (DE)

(*) Notice: Subject to any disclaimer, the term of this patent is extended or adjusted under 35 U.S.C. 154(b) by 245 days.

(21) Appl. No.: 13/067,741

(22) Filed: Jun. 23, 2011

(65) Prior Publication Data

US 2012/0002787 A1  Jan. 5, 2012

(30) Foreign Application Priority Data

Jul. 5, 2010 (DE) .......................... 10 2010 030 939

(51) Int. Cl.
*G01N 23/207* (2006.01)
(52) U.S. Cl.
USPC .......................................................... 378/75
(58) Field of Classification Search
USPC ..................... 378/70–75; 250/390.09, 310
See application file for complete search history.

(56) References Cited

U.S. PATENT DOCUMENTS

| | | | | |
|---|---|---|---|---|
| 4,592,082 | A * | 5/1986 | Pawloski | 378/75 |
| 4,991,191 | A * | 2/1991 | Suryanarayanan | 378/75 |
| 6,327,334 | B1 * | 12/2001 | Murray et al. | 378/75 |

OTHER PUBLICATIONS

Christopher J. Gilmore et al., "High-throughput powder diffraction. I. A new approach to qualitative and quantitative powder diffraction pattern analysis using full pattern profiles", J. Appl. Cryst. (2004), 37, 231-242.

Gordon Barr et al., "PolySNAP3: a computer program for analysing and visualizing high-throughput data from diffraction and spectroscopic sources", J. Appl. Cryst. (2009), 42, 965-974.

Wei Dong et al., "A Quick Method for the Quantitative Analysis of Mixtures. 1. Powder X-Ray Diffraction", Journal of Pharmaceutical Sciences, vol. 97, 2260-2276 (2008).

Steve J. Chipera et al., "FULLPAT: a full-pattern quantitative analysis program for X-ray powder diffraction using measured and calculated patterns", J. Appl. Cryst. (2002), 35, 744-749.

Gordon Barr et al., "SNAP-1D: a computer program for qualitative and quantitative powder diffraction pattern analysis using the full pattern profile", J. Appl. Cryst., vol. 37, pp. 665-668, (2004).

Nicola V.Y. Scarlett et al., "Energy-dispersive diffraction studies of inert anodes", J. Appl. Cryst., vol. 42, pp. 502-512, (2009).

(Continued)

*Primary Examiner* — Irakli Kiknadze
(74) *Attorney, Agent, or Firm* — Paul Vincent

(57) ABSTRACT

A method for automatic determination of the quantitative composition of a powder sample, comprises the following steps: (a) predetermining a list of phases; (b) calculating a theoretical diffraction diagram or theoretical energy-dispersive spectrum; (c) fitting the theoretical diffraction diagram or theoretical energy-dispersive spectrum. In step (a), a list is predetermined which is composed of phases that are actually contained in the powder sample and also phases that are possibly not contained in the powder sample, a threshold value for the phase content is predetermined for each phase, and the following further steps are carried out: (d) elimination of all phases, having phase contents which are below the threshold value, from the list in step (a); (e) repeating steps (b), (c) and (d) with the new list until all phase contents are above their predetermined threshold values; and (f) outputting the composition of the powder sample. This method permits automatic exclusion of amorphous or crystalline phases with phase contents below a user-definable threshold value in profile adjustment methods based on Rietveld or Pawley methods.

10 Claims, 1 Drawing Sheet

(56) References Cited

OTHER PUBLICATIONS

Altomare, A. et al. Journal of Applied Crystallography, vol. 34, Pa. 392-397, (2001).
Hill RJ, Howard CJ "Quantitative phase analysis from neutron powder diffraction data using Rietveld method", J Appl Cryst 20: 467-474, (1987).

I.C. Madsen, N.V.Y. Scarlett "Quantitative Phase Analysis; Powder Diffraction: Theory and Practice", RSC Publishing, ISBN 978-0-85404-231-9, p. 298-331, (2008).
Scarlett, N.V.Y. & Madsen I.C. "Quantification of phases with partial or no known crystal structure", Powder Diffraction, 21(4, 278-284, (2006).

* cited by examiner

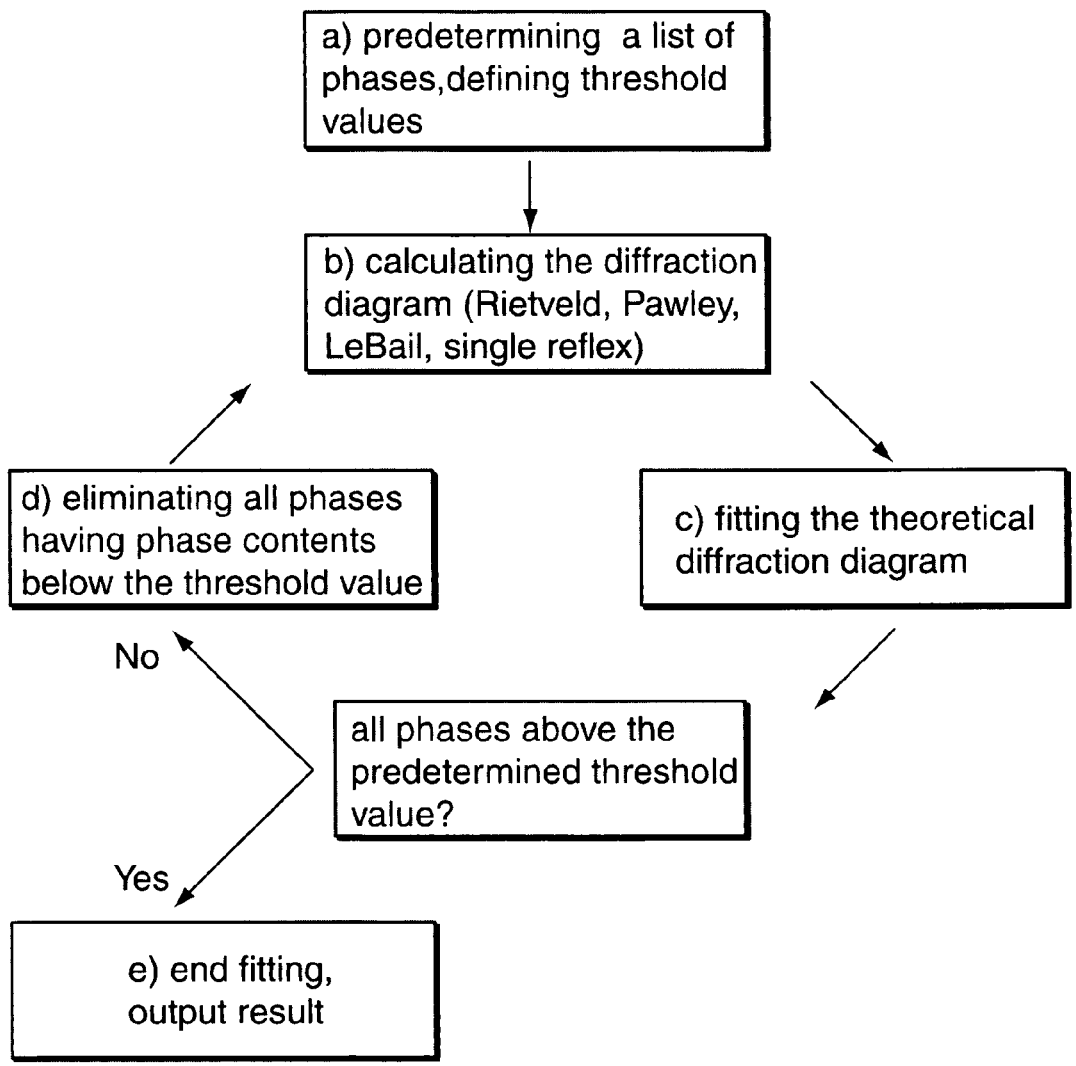

METHOD FOR DETERMINING THE QUANTITATIVE COMPOSITION OF A POWDER SAMPLE

This application claims Paris Convention priority of DE 10 2010 030 939.7 filed Jul. 5, 2010 the complete disclosure of which is hereby incorporated by reference.

BACKGROUND OF THE INVENTION

The invention concerns a method for automatically determining the quantitative composition of a powder sample, which consists of different phase contents of crystalline and/or amorphous phases, from a diffraction diagram recorded by diffractometry from the powder sample or from an energy-dispersive spectrum, the method comprising the following steps:
(a) predetermining a list of phases which are to be allocated to the phase contents in the powder sample;
(b) calculating a theoretical diffraction diagram or theoretical energy-dispersive spectrum based on the phases predetermined in the list in step (a);
(c) fitting the theoretical diffraction diagram or theoretical energy-dispersive spectrum to that of the recorded powder sample by variation of the phase contents of the theoretical diffraction diagram or theoretical energy-dispersive spectrum.

A method of this type is disclosed in an article by Hill R J, Howard C J [1].

I. C. Madsen and N. V. Y. Scarlett [2] give an up-to-date overview of powder-diffractometric methods for quantitative phase analysis.

X-ray diffractometry is used in a plurality of ways for analyzing crystalline (and with certain restrictions also amorphous) components of samples. X-ray radiation is thereby diffracted on crystal planes in the sample. The spatial intensity distribution of the diffracted X-ray radiation, in particular, the position of intensity maxima ("reflexes") gives information e.g. about interlattice plane distances and therefore about the crystal lattice (lattice symmetry) or also about preferred interlattice plane orientations (textures). The basic relationship between interlattice plane distance, angle of incidence and wavelength of X-ray radiation is described by Bragg's law. Procedures based on the Rietveld method are often used for quantification in measurements by X-ray diffractometry. The Rietveld method adjusts a theoretically calculated X-ray diffraction diagram of a polycrystalline substance to a measured X-ray diffraction diagram by means of the mathematical method of least squares. The crystal structure, i.e. the spatial arrangement of the atoms of all existing phases, is required for calculating, in particular, the reflex intensities in the X-ray diffraction diagram. More recent methods based on adjustment of a) individual reflexes, b) the Pawley method or c) the LeBail method use measured intensities instead of calculated intensities, which can be obtained e.g. from measurement of a pure phase (e.g. PONKCS method [3]. This enables quantification of phases, the crystal structure of which is only partially known or not known at all (e.g. amorphous phases).

However, all methods for quantitative analysis of powder samples disclosed up to now only enable quantification of phases which are actually present in the sample. If, however, the refinement model specifies phases which are actually not present in the sample, one still finds phase contents (often >>1%) either as a result of parameter correlations (i.e. inadmissible allocation of intensities to the non-existing phase) or through accidental adjustment of artifacts such as e.g. noise or other profile misfits.

For this reason, the problem arises that the exact qualitative composition of the sample must be known prior to the quantitative analysis.

This causes problems when the composition of the sample fluctuates, e.g. in case of samples from a quarry.

The quantitative analysis therefore requires a pre-scan, wherein, however, for example due to noise, phases are also found which are actually not present in the sample.

It is therefore the underlying purpose of the invention to enable automatic exclusion of amorphous or crystalline phases with phase contents below a user-definable threshold value in profile adjustment methods based on the Rietveld or Pawley methods.

SUMMARY OF THE INVENTION

This object is achieved in accordance with the invention in that, in step (a), a list is predetermined which is composed of phases that are actually contained in the powder sample and also phases that are possibly not contained in the powder sample, a threshold value for the phase content is predetermined for each phase, and the following further steps are carried out:
(d) elimination of all phases having phase contents which are below the threshold value, from the list in step (a);
(e) repeating steps (b), (c) and (d) with the new list until all phase contents are above their predetermined threshold values; and
(f) outputting the composition of the powder sample with the remaining phases and associated phase contents.

This invention enables operation with generalized refinement models which may also contain phases that are not contained in the sample. This is very advantageous for automated data evaluation, since it allows, for the first time, evaluation of samples with variable phase composition. A variable phase composition is basically possible in any field of application, in particular, however in the fields of industrial minerals and minerals and mining.

The essential advantage of this invention is the fact that phase identification (qualitative phase analysis) and quantitative phase analysis are performed in parallel. For this reason, it would be obvious to simply ignore all phases below a threshold value in a simplified method, and to normalize the results to 100% for the remaining phases. The big disadvantage of such a method would be unavoidable parameter correlations which necessarily lead to calculation of inexact (or even extremely wrong) phase contents when actually non-existing phases are also refined. Instead, the inventive method repeats profile adjustment after new determination of the phase composition such that fundamentally more precise results are obtained.

One further particular advantage of this invention is the feature of performing fully automatic phase identification. Since this phase analysis takes into consideration any measured data point, the results are particularly precise. This is in contrast to classical methods, in which only discrete peak positions are compared. Since the profile adjustment methods adjust altered peak positions (e.g. due to mixed crystal formation or measuring errors due to preparation), the danger of confusion with other phases (with different chemism but similar peak positions) is clearly reduced.

One preferred embodiment of the invention is characterized in that the same global phase content threshold value is predetermined for each phase.

In an alternative fashion, an individual phase content threshold value is predetermined for each phase.

In one variant of this embodiment of the inventive method, the threshold value is predetermined for each phase in dependence on the proof limit or the noise threshold of the measuring method that is used.

In the inventive method, a profile adjustment method based on individual reflexes is advantageously applied in step (c). This is advantageous, in particular, for amorphous phases.

In an alternative fashion, a profile adjustment method based on the Rietveld method is applied in the inventive method in step (c).

In an alternative fashion, a profile adjustment method based on the Pawley method is applied in the inventive method in step (c). This is the case whenever the crystal structure of the relevant phase is not known and for this reason the Rietveld method cannot be applied.

Another alternative is use of a profile adjustment method based on the LeBail method in step (c). This is advantageous whenever use of the Pawley method is disadvantageous due to strong correlations between reflex and background parameters.

In the inventive method, the diffraction diagram or energy-dispersive spectrum is preferably recorded by means of X-ray, neutron or electron diffractometry.

The invention also concerns use of the inventive method for quality control, in particular online.

Further advantages of the invention can be extracted from the description and the drawing. The features mentioned above and below may be used individually or collectively in arbitrary combination. The embodiments shown and described are not to be understood as exhaustive enumeration but have exemplary character for describing the invention.

BRIEF DESCRIPTION OF THE DRAWING

FIG. 1 shows a schematic view of the method.

DESCRIPTION OF THE PREFERRED EMBODIMENT

FIG. 1 schematically shows the sequence of the method steps. At first, a phase list is predetermined in step a), which contains those phases which are assumed to be contained in the sample. Moreover, threshold values for phase contents are defined below which the respective phases shall not be taken into consideration.

The diffraction diagram is then calculated in step b).

The theoretical diffraction diagram is then fitted in step c). Subsequent thereto, it is checked whether all phases or phase contents are above the threshold value.

If this should not be the case, step d) follows in which all phases are eliminated, the phase contents of which are below the threshold value.

Steps b) and c) are repeated with the phase list modified in this fashion.

This cycle is repeated until only phases are left, the phase contents of which are above the threshold value. When the automatic examination at the end of step c) shows that this is the case, step e) follows, i.e. output of the result.

LITERATURE

[1] Hill R J, Howard C J (1987) Quantitative phase analysis from neutron powder diffraction data using Rietveld method. J Appl Cryst 20:467-474
[2] I. C. Madsen, N. V. Y. Scarlett (2008): Quantitative Phase Analysis; Powder Diffraction Theory and Practice, RSC Publishing, ISBN 978-0-85404-231-9, p. 298-331.
[3] Scarlett, N. V. Y. & Madsen, I. C. (2006). Quantification of phases with partial or no known crystal structure. Powder Diffraction, 21 (4), 278-284.

I claim:

1. A method for automatic determination of a quantitative composition of a powder sample, having different phase contents of crystalline and/or amorphous phases, from a diffraction diagram recorded by diffractometry from the powder sample or from an energy-dispersive spectrum, the method comprising the steps of:
   a) predetermining a list of phases which are to be allocated to the phase contents in the powder sample, the predetermined list comprising phases that are actually contained in the powder sample as well as phases that may not be contained in the powder sample, wherein a threshold phase content value is set for each phase;
   b) calculating a theoretical diffraction diagram or theoretical energy-dispersive spectrum based on the phases predetermined in the list of step a);
   c) fitting the theoretical diffraction diagram or theoretical energy-dispersive spectrum to that of a recorded powder sample by variation of the phase contents of the theoretical diffraction diagram or theoretical energy-dispersive spectrum;
   d) eliminating all phases having phase contents which are below the threshold value from the list of step a), thereby generating a new list;
   e) repeating steps b), c) and d) until all phase contents are above predetermined threshold values thereof; and
   f) outputting the composition of the powder sample with remaining phases and associated phase contents thereof.

2. The method of claim 1, wherein a same global threshold phase content value is set for each phase.

3. The method of claim 1, wherein individual threshold phase content values are set for each phase.

4. The method of claim 3, wherein the threshold phase content values are predetermined for each phase in dependence on a proof limit or noise threshold of a measuring method that is used.

5. The method of claim 1, wherein a profile adjustment method based on individual reflexes is used in step c).

6. The method of claim 1, wherein a profile adjustment method based on a Pawley method is used in step c).

7. The method of claim 1, wherein a profile adjustment method based on a LeBail method is used in step c).

8. The method of claim 1, wherein a profile adjustment method based on a Rietveld method is used in step c).

9. The method of claim 1, wherein the diffraction diagram or energy-dispersive spectrum is recorded by means of X-ray, neutron or electron diffractometry.

10. Use of the method of claim 1 for quality control or for online quality control.

\* \* \* \* \*